(12) United States Patent
Steenfeldt-Jensen et al.

(10) Patent No.: US 6,547,763 B2
(45) Date of Patent: Apr. 15, 2003

(54) DOSE DISPLAY FOR INJECTION DEVICE

(75) Inventors: Søren Steenfeldt-Jensen, Hornbaek (DK); Peter Møller-Jensen, Hørsholm (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/853,192

(22) Filed: May 11, 2001

(65) Prior Publication Data

US 2001/0053894 A1 Dec. 20, 2001

Related U.S. Application Data

(60) Provisional application No. 60/208,298, filed on May 31, 2000.

(30) Foreign Application Priority Data

May 18, 2000 (DK) .................................. PA 2000 00799

(51) Int. Cl.⁷ ................................................. A61M 5/00
(52) U.S. Cl. ........................................ 604/181; 604/207
(58) Field of Search ........................... 604/181, 186, 604/187, 189, 246, 164.01, 93.01, 200, 207–211

(56) References Cited

U.S. PATENT DOCUMENTS 6,074,372 A * 6/2000 Hansen ....................... 604/211

FOREIGN PATENT DOCUMENTS

| DE | OS 42 08 677 | 9/1993 |
|---|---|---|
| EP | 327 910 | 8/1989 |
| EP | 450 905 | 10/1991 |
| EP | 554 996 | 8/1993 |
| EP | 897 728 | 2/1999 |
| WO | WO 93/07922 | 4/1993 |
| WO | WO 93/11813 | 6/1993 |
| WO | WO 98/56436 | 12/1998 |
| WO | WO 89/07463 | 8/1999 |

* cited by examiner

*Primary Examiner*—Anhtuan T. Nguyen
*Assistant Examiner*—Ann Y. Lam
(74) *Attorney, Agent, or Firm*—Marc A. Began, Esq.; Richard W. Bork, Esq.; Reza Green, Esq.

(57) ABSTRACT

A dose display for a medicine administration device in which rotation of a dose setting actuator (22) is transmitted to a display means comprises a flexible disc (23) carrying numbers in a band along its perimeter, which numbers are in accordance with the set dose presented in a window in a wall of the device to show said dose. During its rotation the disc (23) is deflected to follow an inner contour of the device to attain a cylindrical shape having a generatrix extending in the axial direction of the injection device and perpendicular to the axis of rotation of the disc.

13 Claims, 2 Drawing Sheets

DOSE DISPLAY FOR INJECTION DEVICE

Figure 1:
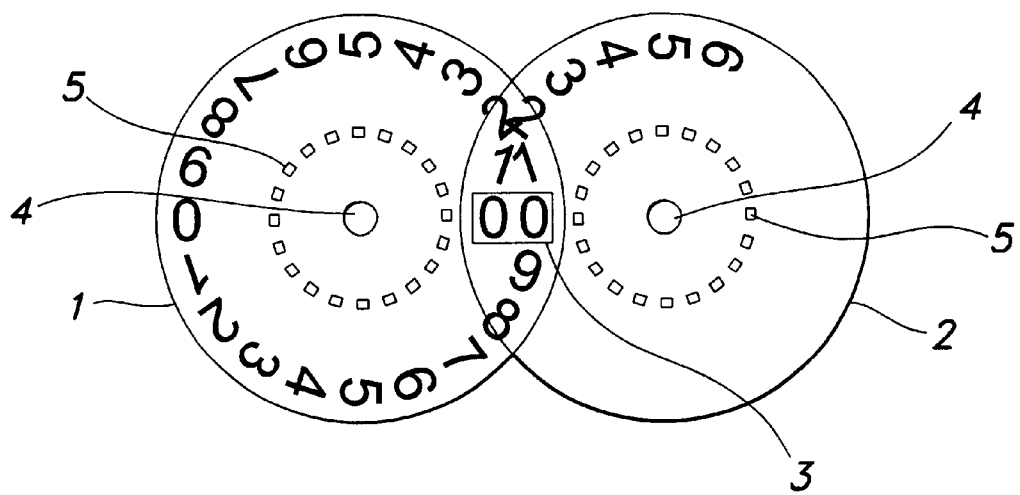

This Application claims the benefit of No. 60/208,298, filed May 31, 2000.

The invention relates to injection devices of the kind by which set doses are apportioned from a cartridge containing a volume of medicine sufficient for several doses. Such devices are often designated as "pens" and may be designed as a pen to be carried by a clip in a pocket the same way as a fountain pen. However, the injection devices need not necessarily have a circular cross section but may have an elongated tubular shape with a more or less rectangular cross section. More specifically the invention relates to a display for such an injection device.

The dose is set by operating a dose setting actuator and the set dose is shown on a display either by a pointer pointing at a number indicating the size of the dose or by a number being presented in a window or on an electronic display.

As the size of the injection device commonly is minimised to make it easy for the user to bring the device with him in a pocket the restricted size of the device sets a limit to the size and thereby to the readability of the numbers in the display.

In EP 327910 a scale shoving numbers up to 18 is provided along a perimeter of the device. A pointer points at this scale and by doses larger than 20 units which are set by rotating the dose setting element more than 360°, the size of the dose must be calculated by reading and adding the showing on to different scales. The device only allows settings in step of two units, i.e. 10 numbers are printed along the perimeter and the maximum size of each number consequently is smaller than a tenth of the perimeter.

The two-scale reading of the dose is avoided where the numbers are printed along a helical drum surface of which the part carrying the number indicating the set dose is presented in a window as in 608343, however the numbers of steps per turn of the dose setting member still puts a limit on the height of each written number, if the number of steps per turn are low the width of the numbers will be correspondingly small.

In EP 554 996 numbers having a height of up to one tenth of the perimeter of the injection device without any restrictions of the width of the digits of the number is obtained by using a counter having a number drum for each digit, i.e. "1" counting drum and a "10" counting drum. If wanted a "100" counting drum may be added an so on. The numbers on the counting drums may all be up to one tenth of the perimeter of the drum or $\frac{1}{10} \times \pi \times d$ where d isx the diameter of the counting drum which almost corresponds to the inner diameter of the injection device.

If an electronic display is used the mechanical movement of the dose setting parts does not set any limit to the size of the display. However, the mechanically working displays are appropriate especially for disposable syringes as the display may be made from the same materials as are the syringe whereby the syringe may easier be disposed of in a way which is environmentally acceptable.

Consequently it is an object of the invention to provide a mechanical display by which still larger numbers are allowed.

A dose display, in which rotation of a dose setting actuator is transmitted to a display means carrying numbers which are in accordance with the set dose presented in a window in a wall of an injection device, is according to the invention characterised in that it has at least one flexible disk which is driven by the dose setting actuator and which in a band along its perimeter carries numbers which can, depending on the rotational position of the disc, be presented in the window to show a set dose, the disc being deflected to follow an inner contour of the device to attain a cylindrical shape with a generatrix extending in the axial direction of the injection device and perpendicular to the axis of rotation of the disc.

If a disc is folded so that diametrical opposite points of its perimeter just meet, each digit along the perimeter can be made about three times as high as corresponding digits written on a drum having a diameter corresponding to the diameter of the tube formed by the folded disc. If the diametrical opposite edges are allowed to overlap the digits may be still higher.

Two discs may be placed with their axis parallel and in a distance less than the diameter of the discs away from each other so that the discs overlap each other to make it possible to show a two-digit number. In that case the disc overlapping the other must be transparent. Alternatively the overlapping disc can be provided with windows wherein the showing of the digits on the overlapped disk can be seen. However, this construction will weaken the disc.

The discs may be provided with a perforation along a circle concentric with the digit band. This perforation is designed to be engaged by transporting sprockets in order to rotate the disk in accordance with rotation of the dose setting member. The perforation may appropriately comprise a number of holes at least corresponding to the number of digits along the perimeter of the disc.

In a preferred embodiment one foldable disk is fixed to the dose setting element to rotate with this element an the numbers from zero to the maximum dose which can be set are printed consecutively along the perimeter of the foldable disk to be presented in a window to indicate the set dose.

Figure 2:
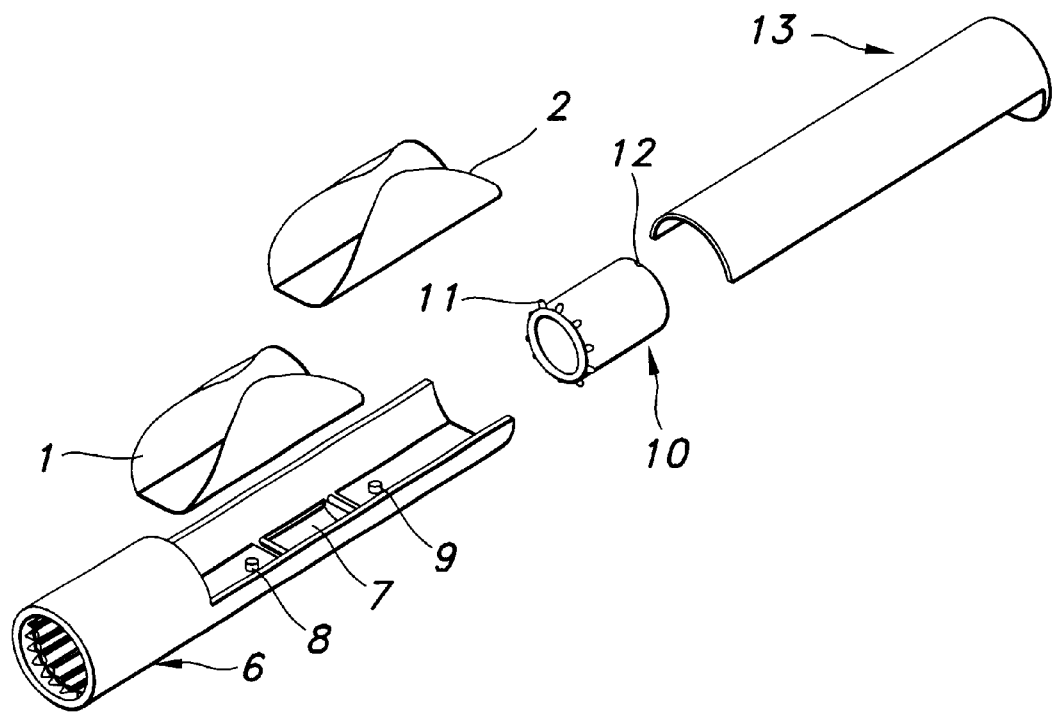
Figure 3:
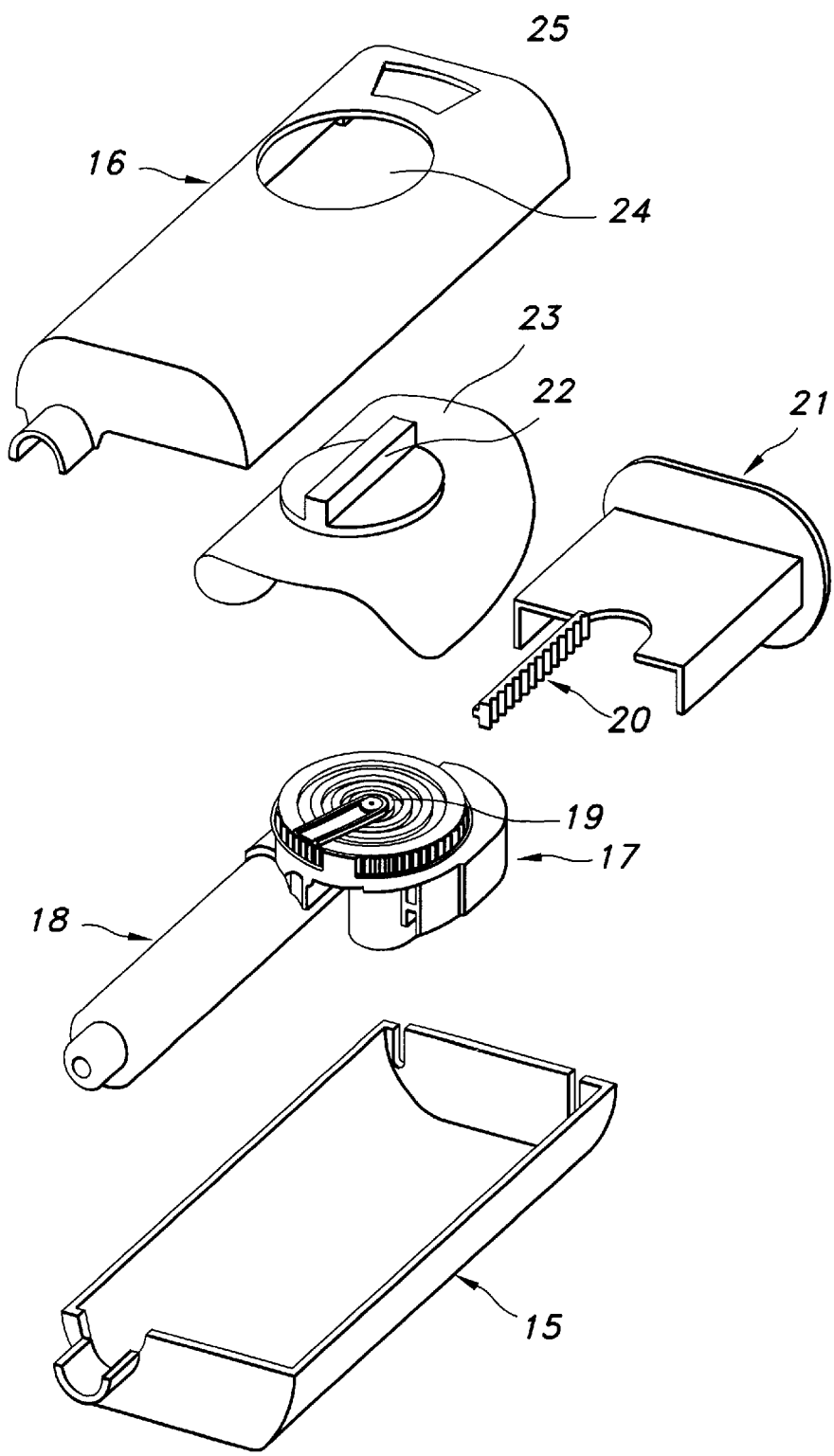

In the following the invention is described in further details with references to drawing, wherein FIG. 1 shows schematically a display formed by two foldable disks, FIG. 2 shows schematically in an exploded perspective how the disks of FIG. 1 can be placed in a device and be driven by a sprocket wheel, FIG. 3 shows another device in which only one foldable disk is used.

FIG. 1 shows schematically a two-digit display device comprising a disc 1 showing the "ones" and a disc 2 showing the "tens". The discs have consecutive numbers written along their perimeter. The shown "ones" disc 1 has the numbers from 0 to 9 written in two consecutive series, each series of number extending over half the perimeter. The other disc 2 showing the "tens" has a number of numbers written depending on the maximum dose which it is intended to make readable in a display window 3. In FIG. 1 the numbers from 0 to 6 are shown making the display able to show doses from 0 to 69 units. The numbers on the "tens" disc 2 has the same size as the numbers of the "ones" disc 1 and each number takes up ½₀ of the perimeter. Both discs 1 and 2 are provided with a centre hole 4 by which the discs can be journaled on a pair of pivot pins placed at a distance smaller than the diameter of the discs away from each other. Thereby the discs 1 and 2 will overlap each other and the digits of the disc placed to the left will in the display be shown to the right of the digits of the disc placed to the right. The discs are made of a transparent material and consequently the digits of the disc overlapped by the other will be visible through the transparent disc. Along a circle concentric with the perimeter each disc is provided with sprocket holes 5 by which the disc by a sprocket wheel can be rotated about the pivot pin through its centre hole 5. FIG. 2 shows schematically a part of a pen shaped device wherein the disks in FIG. 1 can be mounted. A housing part 6 is provided with a window 7 wherein numbers along the perimeter of the foldable discs 1 and 2 can be shown when these disks are mounted with their centre holes fitting over a pair of pivot pins 8 and 9 provided on the inner wall of the housing part 6 on each side of the window 7. A sprocket drum 10 having ten sprockets 11 spaced along the perimeter of a first end and one sprocket 12 at the perimeter of the other end is mounted in the device partly encompassed by the disks and with its sprockets 11 engaging the sprocket holes 5 in the "ones" counting disk 1. The other end of the sprocket drum 10 lies opposite the sprocket holes 5 of the "tens" counting disk 2 so that the one sprocket 12 at this second end engages a sprocket hole in this disk 2 when the "ones" counting disk 1 shows a "9" in the window 3. When the showing of the "ones" counting disk 1 in the window 3 changes from "9" to "0" the "tens" counting disk is advanced to shift its showing from one of the numbers along its perimeter to the subsequent number. The sprocket drum 10 is coupled to a not shown dose-setting member in the device to be appropriate rotated when this dose-setting member is operated. After mounting of the disks 1 and 2 the shown part of the device is closed by another part 13 fitting onto the part 6.

FIG. 3 shows another embodiment of a device having a flexible dose display disk. The shown device, which is of the type wherein the slim design is left in favour of a short device, has a housing comprising a lower part 15 and an upper part 16 encompassing a dose setting and injection module 17 by which a dose can be apportioned from an ampoule 18.

The dose setting and injection module 17 can be operated for dose setting by transmitting a rotational movement to the module at the centre 19 of the module, and a set dose can be injected by transmitting a force to the module 17 through a rack 20 carried by an injection button 21 which is mounted in the housing.

A rotatable dose setting grip 22 it mounted to the centre 19 of the dose setting and injection module 17. A flexible disc 23 is mounted to the dose setting grip 22 concentric with this grip to be rotated with this grip. Due to its flexibility the disc will follow he inner contour of the parts 15 and 15 forming the housing and. The upper part 16 of the housing is provided with a cut out 24 for the dose setting grip 22 and with a window 25 through which not shown numbers along the perimeter of the flexible disc 23 can be read. The not shown numbers on the disc shows the dose set by rotating the grip 22. The module 17 may further be so designed that the grip is rotated back to its zero position when a set dose is injected by operation of the injection button 21 and the disc 23 will consequently currently in the window 25 show how much of the set dose is left to inject.

What is claimed is:

1. A medical device having a dosage display, the medical device comprising:
    a housing having:
        a longitudinal dimension, a window, and an inner contour having a surface shaped to deflect a flexible disc in a generally cylindrical manner,
    a dose setting actuator,
    a display means carrying digits that, in accordance with the set dose, are shown in the window, wherein:
        the display means comprises at least one rotatable flexible disc that is driven by the dose setting actuator and carries numbers along its perimeter that can, depending on the rotational position of the disc, be presented in the window to show a set dose, the disc being deflected to follow the inner contour of the housing to attain a cylindrical shape having a generatrix extending in the longitudinal direction of the injection device and perpendicular to the axis of rotation of the disc.

2. The device according to claim 1, wherein the flexible disc is mounted to the dose setting actuator to rotate with the actuator.

3. The device according to claim 1, wherein the display means comprises a second disc also having digits located on an outer perimeter, the two discs placed with their axes of rotation parallel and in a distance less than the diameter of the discs away from each other so that the discs overlap each other to make it possible to show a two-digit number created by one digit from each disc, the disc overlapping the other being transparent to allow reading of the digits on the overlapped disc through the overlapping disc.

4. The device according to claim 3, wherein the discs are each provided with perforations along a circular path concentric with the perimeter formed by the digits, the perforations being designed to be engaged by transporting sprockets on a drum driven by the dose setting actuator in order to rotate the disks accordance with the dose set.

5. The device according to claim 4, wherein the perforations comprise a number of sprocket holes corresponding to the number of digits along the perimeter of the disc.

6. A medical device with a dosage display, the device comprising:
    a housing having a window and an inner surface with a contour,
    a dose setting mechanism having a dose setting member to set a dose, and
    a display means having numbers, wherein:
        the display means comprises at least one rotatable flexible disc, which is driven by the dose setting mechanism,
        the disc carries digits along an outer perimeter, and
        the disc is deflected to follow the inner contour of the housing to attain a cylindrical shape and displays at least a portion of the numbers in the window, the displayed numbers corresponding to the set dose.

7. The device according to claim 6, wherein the flexible disc is mounted to the dose setting mechanism to rotate with the dose setting member.

8. The device according to claim 6, wherein the display means comprises a second disc with digits along an outer perimeter, the two discs placed parallel to each other and at a distance apart that is less than the diameter of the discs so that the discs overlap each other to make it possible to show a two-digit number comprised of one digit from each disk, at least the disc overlapping the other being transparent to allow reading of the digits on the overlapped disc through the overlapping disc, the two digit number corresponding to the set dose.

9. The device according to claim 8, further comprising a drum containing sprockets, the drum being driven by the dose setting mechanism, and wherein the discs are each provided with perforations along a circle concentric with the digit perimeter, the perforations engaging the sprockets on the drum.

10. The device according to claim 9, wherein the perforations comprise a number of sprocket holes, each hole corresponding to a single digit along the perimeter of the disc.

11. A dosage display comprising:

a window;

a flexible rotatable disc carrying numbers along a perimeter;

a means for deflecting the disc in a generally cylindrical manner; and a means for rotating the disc to display a number from the disc in the window, the number corresponding at least partially to a set dose.

12. The dosage display of claim 11, wherein the means for deflecting the disc comprises a means for deflecting the disk so that the resulting cylindrical shape has a generatrix extending in a direction perpendicular to the axis of rotation of the disc.

13. The dosage display of claim 12, wherein the generatrix extends in a direction parallel to the longitudinal direction of the housing.

* * * * *